US010195396B2

United States Patent
Clark et al.

(10) Patent No.: US 10,195,396 B2
(45) Date of Patent: *Feb. 5, 2019

(54) CATHETER WITH SERIALLY CONNECTED SENSING STRUCTURES AND METHODS OF CALIBRATION AND DETECTION

(71) Applicant: BIOSENSE WEBSTER (ISRAEL) LTD., Yokneam (IL)

(72) Inventors: Jeffrey L. Clark, Castaic, CA (US); George Kamin, Arcadia, CA (US); Mark Stanley, Seal Beach, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/865,215

(22) Filed: Jan. 8, 2018

(65) Prior Publication Data

US 2018/0126123 A1 May 10, 2018

Related U.S. Application Data

(63) Continuation of application No. 15/351,346, filed on Nov. 14, 2016, now Pat. No. 9,861,785, which is a
(Continued)

(51) Int. Cl.
*A61B 5/00* (2006.01)
*A61M 25/01* (2006.01)
(Continued)

(52) U.S. Cl.
CPC ........... *A61M 25/0127* (2013.01); *A61B 5/05* (2013.01); *A61B 5/062* (2013.01); *A61B 5/065* (2013.01);
(Continued)

(58) Field of Classification Search
CPC ........... A61B 5/05; A61B 5/065; A61B 5/062; A61M 25/0127
See application file for complete search history.

(56) References Cited

U.S. PATENT DOCUMENTS

| 5,391,199 A | 2/1995 | Ben-Haim |
| 5,568,809 A | 10/1996 | Ben-haim |

(Continued)

FOREIGN PATENT DOCUMENTS

| EP | 2338411 A1 | 6/2001 |
| EP | 1184684 A2 | 3/2002 |

(Continued)

OTHER PUBLICATIONS

Extended European Search Report dated Aug. 12, 2014 in EP application No. 14167950.6, 7 pages.
(Continued)

*Primary Examiner* — Joel Lamprecht
(74) *Attorney, Agent, or Firm* — Lewis Roca Rothgerber Christie LLP

(57) ABSTRACT

A catheter is responsive to external and internal magnetic field generators for generating signals representing position and pressure data, with a reduced number of sensing coil leads for minimizing lead breakage and failure. The catheter includes a flexible joint with pressure sensing and position coils, at least pair of a pressure sensing coil and a position coil are serially connected. Methods of calibrating a catheter for position and pressure sensing, and detecting magnetic field interference with one catheter by another catheter or other metal or ferrous object advantageously use signals between two sets of sensors as a "back up" or "error check".

20 Claims, 3 Drawing Sheets

Related U.S. Application Data continuation of application No. 14/960,273, filed on Dec. 4, 2015, now Pat. No. 9,492,639, which is a continuation of application No. 13/732,324, filed on Dec. 31, 2012, now Pat. No. 9,204,841.

(51) Int. Cl.

| | | |
|---|---|---|
| *A61B 5/06* | (2006.01) | |
| *A61B 18/14* | (2006.01) | |
| *A61B 18/12* | (2006.01) | |
| *A61B 5/05* | (2006.01) | |
| *A61M 25/00* | (2006.01) | |
| *A61B 18/00* | (2006.01) | |
| *A61B 90/00* | (2016.01) | |
| *A61B 34/20* | (2016.01) | |

(52) U.S. Cl.
CPC .............. *A61B 5/6852* (2013.01); *A61B 5/72* (2013.01); *A61B 18/1206* (2013.01); *A61B 18/1492* (2013.01); *A61B 5/6885* (2013.01); *A61B 2018/00357* (2013.01); *A61B 2018/00577* (2013.01); *A61B 2034/2051* (2016.02); *A61B 2090/065* (2016.02); *A61M 2025/0002* (2013.01)

(56) References Cited

U.S. PATENT DOCUMENTS

| | | | |
|---|---|---|---|
| 5,752,513 A | 5/1998 | Acker et al. | |
| 6,063,022 A | 5/2000 | Ben-Haim | |
| 6,161,032 A | 12/2000 | Acker | |
| 6,239,724 B1 | 5/2001 | Doron et al. | |
| 6,332,089 B1 | 12/2001 | Acker et al. | |
| 6,427,314 B1 | 8/2002 | Acker | |
| 6,484,118 B1 | 11/2002 | Govari | |
| 6,574,492 B1 | 6/2003 | Ben-Haim et al. | |
| 6,593,884 B1 | 7/2003 | Gilboa et al. | |
| 6,600,948 B2 | 7/2003 | Ben-Haim et al. | |
| 6,618,612 B1 | 9/2003 | Acker et al. | |
| 6,690,963 B2 | 2/2004 | Ben-Haim et al. | |
| 6,833,814 B2 | 12/2004 | Gilboa et al. | |
| 6,892,091 B1 | 5/2005 | Ben-Haim et al. | |
| 6,947,788 B2 | 9/2005 | Gilboa et al. | |
| 7,555,330 B2 | 6/2009 | Gilboa et al. | |
| 8,380,276 B2 | 2/2013 | Schultz | |
| 8,437,832 B2 | 5/2013 | Govari et al. | |
| 9,204,820 B2 | 12/2015 | Clark et al. | |
| 9,204,841 B2* | 12/2015 | Clark | A61B 5/062 |
| 9,492,639 B2* | 11/2016 | Clark | A61B 5/062 |
| 9,861,785 B2* | 1/2018 | Clark | A61M 25/0127 |
| 2002/0065455 A1 | 5/2002 | Ben-Haim et al. | |
| 2002/0165448 A1 | 11/2002 | Ben-Haim et al. | |
| 2003/0120150 A1 | 6/2003 | Govari | |
| 2004/0068178 A1 | 4/2004 | Govari | |
| 2007/0100332 A1 | 5/2007 | Paul et al. | |
| 2009/0093806 A1 | 4/2009 | Govari et al. | |
| 2009/0138007 A1 | 5/2009 | Govari et al. | |
| 2009/0306650 A1 | 12/2009 | Govari et al. | |
| 2010/0210938 A1 | 8/2010 | Verard et al. | |
| 2011/0066029 A1 | 3/2011 | Lyu et al. | |
| 2011/0196397 A1 | 8/2011 | Frantz et al. | |
| 2012/0108988 A1 | 5/2012 | Ludwin et al. | |
| 2014/0187916 A1 | 7/2014 | Clark et al. | |

FOREIGN PATENT DOCUMENTS

| | | |
|---|---|---|
| EP | 1743575 A2 | 1/2007 |
| EP | 1878384 A2 | 1/2008 |
| EP | 2047797 A2 | 4/2009 |
| EP | 2130508 A2 | 12/2009 |
| EP | 2196143 A1 | 6/2010 |
| EP | 2279692 A2 | 2/2011 |
| EP | 2462869 A1 | 6/2012 |
| EP | 2505227 A1 | 10/2012 |
| WO | WO9605768 A1 | 2/1996 |
| WO | 2012098551 A1 | 7/2012 |
| WO | 2012150567 A1 | 11/2012 |

OTHER PUBLICATIONS

Extended European Search Report dated Feb. 27, 2014 for European Application No. EP 13199537.5, 7 pags.

Partial European Search Report dated Mar. 11, 2014 for EP Application No. 13199522.7, 5 pages.

\* cited by examiner

CATHETER WITH SERIALLY CONNECTED SENSING STRUCTURES AND METHODS OF CALIBRATION AND DETECTION

CROSS-REFERENCE TO RELATED APPLICATION(S)

This application is a continuation of and claims priority to and the benefit of U.S. application Ser. No. 15/351,346 filed Nov. 14, 2016 and issued as U.S. Pat. No. 9,861,785, which is a continuation of Ser. No. 14/960,273 filed Dec. 4, 2015 and issued as U.S. Pat. No. 9,492,639, which is a continuation of U.S. application Ser. No. 13/732,324, filed Dec. 31, 2012 and issued as U.S. Pat. No. 9,204,841, the entire contents of all of which are incorporated herein by reference.

FIELD OF INVENTION

The present invention relates to catheters, particularly catheters with location/orientation and pressure sensing capabilities.

BACKGROUND OF INVENTION

In some diagnostic and therapeutic techniques, a catheter is inserted into a chamber of the heart and brought into contact with the inner heart wall. For example, in intracardiac radio-frequency (RF) ablation, a catheter having an electrode at its distal tip is inserted through the patient's vascular system into a chamber of the heart. The electrode is brought into contact with a site (or sites) on the endocardium, and electrical activity in the heart chamber is detected by the electrode. Moreover, RF energy may be applied through the catheter to the electrode in order to ablate the heart tissue at the site.

Catheters for mapping and/or ablation typically carry one or more magnetic position sensors for generating signals that are used to determine position coordinates of a distal portion of catheter. For this purpose, magnetic field generators are driven to generate magnetic fields in the vicinity of the patient. Typically, the field generators comprise coils, which are placed below the patient's torso at known positions external to the patient. These coils generate magnetic fields that are sensed by the magnetic position sensor(s) carried in the catheter. The sensor(s) generate electrical signals that are passed to a signal processor via leads that extend through the catheter.

Proper contact between the electrode and the endocardium is necessary in order to achieve the desired diagnostic function and therapeutic effect of the catheter. Excessive pressure, however, may cause undesired damage to the heart tissue and even perforation of the heart wall. For pressure sensing, a catheter typically carries a miniature transmitting coil and three sensing coils on opposing portions of a flexibly-jointed distal tip section. The transmitting coil is aligned with the longitudinal axis of the catheter and three sensing coils are also aligned with the longitudinal axis but positioned at an equal distance from the transmitting coil, and at equally-spaced radial positions about the longitudinal axis of the catheter. The miniature transmitting coil generates a magnetic field sensed by the three sensing coils which generate signals representative of axial displacement and angular deflection between the opposing portions of the distal tip section.

The axes of the sensing coils are parallel to the catheter axis (and thus to one another, when the joint is undeflected). Consequently, the sensing coils are configured to output strong signals in response to the field generated by the miniature field generator. The signals vary strongly with the distances of the coils. Angular deflection of the distal portion carrying the miniature field generator gives rise to a differential change in the signals output by sensing coils, depending on the direction and magnitude of deflection, since one or two of these coils move relatively closer to the field generator. Compressive displacement of the distal portion gives rise to an increase in the signals from all of three sensing coils. Prior calibration of the relation between pressure on distal portion and movement of joint may be used by processor in translating the coil signals into terms of pressure. By virtue of the combined sensing of displacement and deflection, the sensors read the pressure correctly regardless of whether the electrode engages the endocardium head-on or at an angle.

With position sensing and pressure sensing, a conventional catheter may carry six leads, one for each of the three position sensing coils and the three pressure sensing coil, with each lead being a twisted pair of wires. Leads are time-consuming and expensive to manufacture and install. Moreover, the leads occupy space in the space-constrained catheter tip and are susceptible to breakage. A reduction in the number of leads used in the catheter and/or their lengths would provide a number of benefits, including reduced catheter production time, increased total catheter yield, and reduced production costs.

Some catheterization procedures require the use of a second catheter in close proximity to a first catheter. Shaft Proximity Interference ("SPI") occurs when metal components of the second catheter disturb sensing coils in the first catheter. For example, where a pressure sensing coil reacts to changes in the magnetic field due to errant magnetic interference by an adjacent catheter instead of physical distortion of a distal tip due to tissue contact, signals from the coil can mislead an operator relying a catheterization system processing those signals.

Accordingly, it is desirable to provide a catheter with combined or simplified position and pressure sensing capabilities for reducing the number of sensor coil leads and/or their lengths. It is also desirable to provide a catheter capable of recognizing distortions in magnetic fields caused by factors other than physical distortion of the distal tip due to tissue contact.

SUMMARY OF THE INVENTION

The present invention is directed to a catheter responsive to external and internal magnetic field generators for generating position data to determine position of the catheter within a sensing volume of magnetic fields and pressure data to determine pressured exerted on a distal end of the catheter when engaged with tissue, with a reduced number of sensing coil leads for minimizing lead breakage and failure.

In one embodiment, the catheter includes a distal section adapted for engagement with patient tissue, where the distal section has a proximal portion, a distal portion and a flexible joint. Either of the proximal portion or the distal portion carries an internal magnetic field generator and the other of the proximal portion or the distal portion carries a plurality of first sensing coils and a plurality of second sensing coils, where each of the first sensing coils is axially aligned with the field generator and sensitive to the internal magnetic field generator for generating signals representative of pressure exerted on the distal section, and where each of the second sensing coils is mutually orthogonal to each other and sensitive to each of a plurality of external magnetic field generators for generating signals representative of position of the distal section, where at least one first sensing coil and one second sensing coil are connected to each other by a lead.

In one embodiment, there are three first sensing coils and two second sensing coils.

In one embodiment, the first sensing coils are adapted to generate signals representative of pressure exerted on the distal section and the second sensing coils are adapted to generate signals representative of position of the distal section.

In one embodiment, a first sensing coil is also sensitive to each of the external magnetic field generators for generating signals representative of position of the distal section.

In one embodiment, there are a first pair of first and second sensing coils connected by one lead and a second pair of first and second sensing coils connected by a second lead.

In one embodiment, the flexible joint includes a resilient member adapted to allow axial displacement and angular deflection between the proximal and distal portions of the distal section.

In one embodiment, each magnetic field is distinguishable by frequency, phase and/or time.

The present invention is also directed to a method of calibrating a catheter for position and pressure sensing and a method of detecting magnetic field interference with one catheter by another catheter or other metal or ferrous object. The present invention advantageously uses signals from the sensors Sx and Sy as a "back up" or "error check". A pressure calibration is performed on the catheter during manufacturing and production. By identifying deformation characteristics of the distal section, applying known magnitudes of force on the distal section portion at a variety of selected angles (e.g., compressive loads, axial loads, etc.) and measuring axial displacement and angular deflection, a calibration file on the signals that may be generated by pressure sensors in response to the magnetic field generated by the internal field generator MF is compiled as a first file and stored in memory. Simultaneously, a calibration file on the signals that may be generated by position sensors in response to the magnetic field generated by the internal field generator MF is compiled as a second file and stored in memory. While the catheter is in use in a patient's body, signals from the pressure sensors in response to internal field generator MF are referenced against the first file stored in memory to obtain axial displacement and angular deflection data for outputting catheter pressure data to the operator. Advantageously, signals from positions that include signals in response to the internal field generator MF are referenced against the second file for detecting and identifying discrepancies. If a discrepancy is determined, providing an indication to user of the discrepancy.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

The present invention is directed to a system and catheter for cardiac catheterization, where the catheter has a sensing assembly that provides signals representative of both position of the catheter and pressure exerted on a distal section of the catheter when it engages tissue. Compared to conventional position sensing assemblies and pressure sensing assemblies, sensing assemblies of the catheter are advantageously configured with serially-wired sensing structures to reduce the number of leads and/or their lengths for a simplified catheter structure that minimizes the risk of damaged or broken leads.

Figure 1:
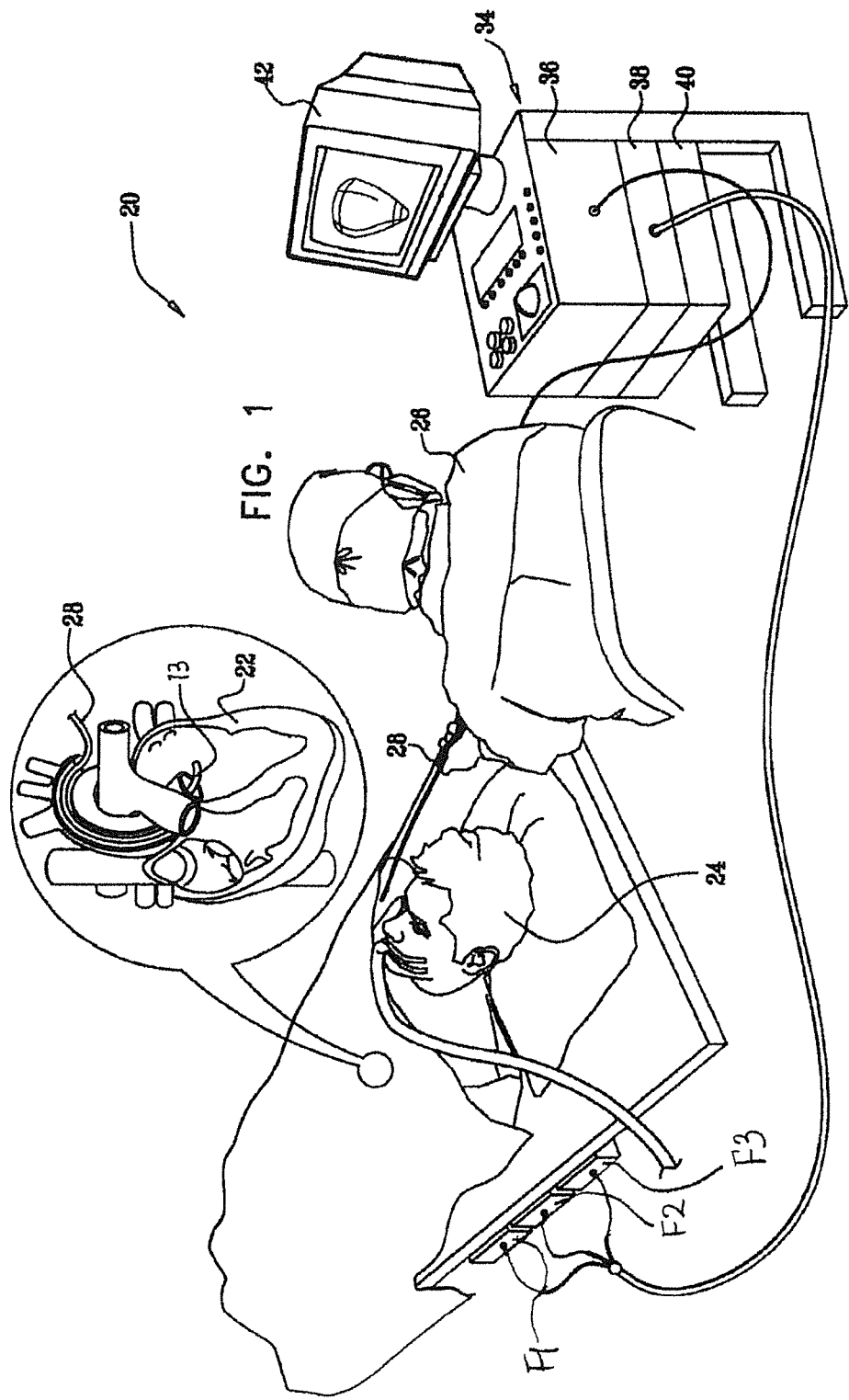
FIG. 1 is a schematic, pictorial illustration of a catheter-based medical system, in accordance with an embodiment of the present invention.
Figure 2:
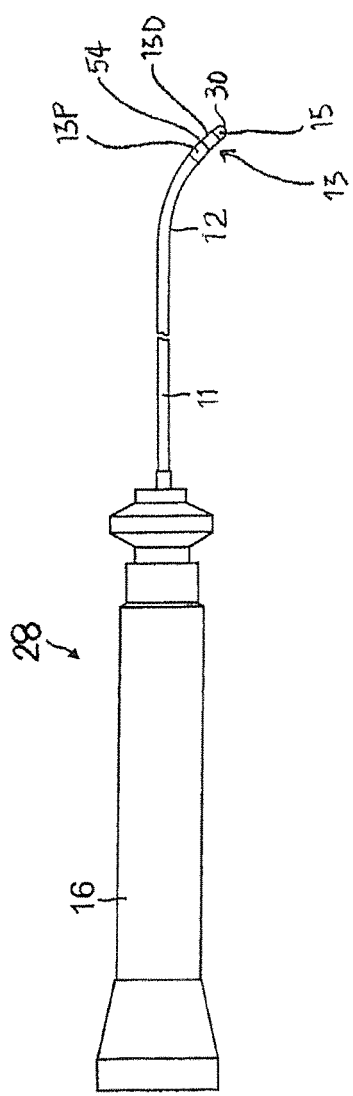
FIG. 2 is a side view of a catheter for use with the system of FIG. 1, in accordance with an embodiment of the present invention.

FIG. 1 is a schematic, pictorial illustration of a conventional system 20 for cardiac catheterization as known in the art. System 20 may be based, for example, on the CARTO™ system, produced by Biosense Webster Inc. (Diamond Bar, Calif.). This system comprises an invasive probe in the form of a catheter 28 and a control console 34. In the embodiment described hereinbelow, it is assumed that catheter 28 is used in ablating endocardial tissue, as is known in the art. Alternatively, the catheter may be used, mutatis mutandis, for other therapeutic and/or diagnostic purposes in the heart or in other body organs. As shown in FIG. 2, the catheter 28 comprises an elongated catheter body 11, a deflectable intermediate section 12, a distal section 13 carrying at least a tip electrode 15 on its distal tip end 30, and a control handle 16.

An operator 26, such as a cardiologist, inserts catheter 28 through the vascular system of a patient 24 so that a distal section 13 of the catheter enters a chamber of the patient's heart 22. The operator advances the catheter so that a distal tip 30 of the catheter engages endocardial tissue 70 at a desired location or locations. Catheter 28 is connected by a suitable connector at its proximal end to console 34. The console may comprise a radio frequency (RF) generator, which supplies high-frequency electrical energy via the catheter for ablating tissue in the heart at the locations engaged by the distal section 13. Alternatively or additionally, the catheter and system may be configured to perform other therapeutic and diagnostic procedures that are known in the art.

Figure 3:
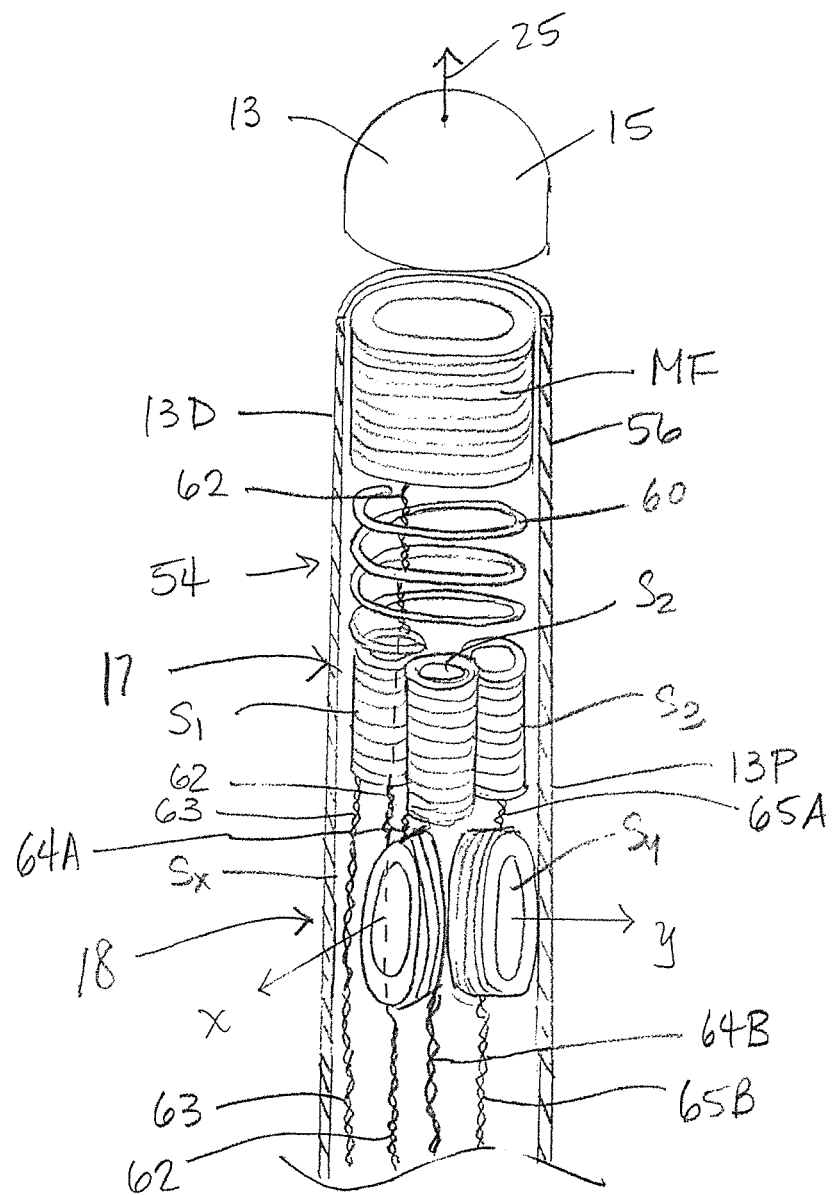
FIG. 3 is a schematic, cutaway view showing details of the distal section of the catheter of FIG. 2.

Console 34 uses magnetic sensing to determine pressure and position data, including (i) axial displacement and angular deflection of the distal section 13 due to pressure from contact with endocardial tissue 70, and (ii) position coordinates of the distal section 13 in the heart. For the purpose of generating pressure data, including axial displacement and angular deflection of the distal section 13 of the catheter 28, the driver circuit 38 in console 34 drives a miniature magnetic field generator MF housed in a distal portion 13D of the tip section 13, as shown in FIG. 3. In the disclosed embodiment, the field generator MF comprises a coil whose axis is aligned with the Z axis coaxial with a longitudinal axis 25 of the catheter.

Figure 4:
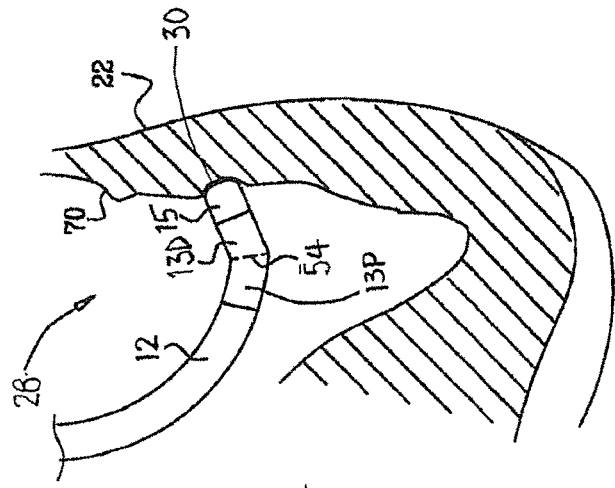
FIG. 4 is a schematic detail view showing the distal section of FIG. 3 in contact with endocardial tissue.

For detecting and measuring pressure, the distal section 13 has a proximal portion 13P and a distal portion 13D which are connected to each other by a flexible and elastic joint 54 which may be constructed of any suitable material(s) with the desired flexibility and strength. The resilient joint 54 permits a limited range of relative movement between the portions 13P and 13D in response to forces exerted on the distal section 13. Such forces are encountered when the distal tip end 30 is pressed against the endocardium during an ablation procedure. As shown in FIG. 4, the distal end 30 of catheter 28 is in contact with endocardium 70 of heart 22, in accordance with an embodiment of the present invention. Pressure exerted by the distal tip end 30 against the endocardium deforms the endocardial tissue slightly, so that the tip electrode 15 contacts the tissue over a relatively large area. Since the electrode engages the endocardium at an angle, rather than head-on, the distal portion 13D bends at joint 54 relative to the proximal portion 13P. The bend facilitates optimal contact between the electrode 15 and the endocardial tissue 70.

As shown in FIG. 3, the joint 54 comprises an outer tubing 56 which may be the outer tubing 55 of the distal section 13 which is constructed of a flexible, insulating material, such as Celcon®, Teflon®, or heat-resistant polyurethane. Or, the tubing 56 may be of a material specially adapted to permit unimpeded bending and compression of the joint. (This material is cut away in FIG. 3 in order to expose the internal structure of the catheter.) The distal section 13D is typically relatively rigid, by comparison with the remainder of the catheter.

The joint 54 further comprises a resilient coupling member 60, such as a coil spring, or a tubular piece of an elastic material with a helical cut along a portion of its length. For example, the coupling member may comprise a polymer, such as silicone, polyurethane, or other plastics, or a superelastic alloy, such as nickel titanium (Nitinol). The helical cut causes the tubular piece to behave like a spring in response to forces exerted on distal portion 13D. Further details regarding the fabrication and characteristics of this sort of coupling member are presented in U.S. Publication No. 2009/0306550, which is assigned to the applicant of the present patent application and whose disclosure is incorporated herein by reference. Alternatively, the coupling member may comprise any other suitable sort of resilient component with the desired flexibility and strength characteristics.

The stiffness of the coupling member 60 determines the range of relative movement between distal portions 13P and 13D in response to forces exerted on the distal portion 13D. Such forces are encountered when the distal tip end 30 is pressed against the endocardium during a mapping and/or ablation procedure. The desired pressure for good electrical contact between the distal portion 13D and the endocardium during ablation is on the order of 20-30 grams. The coupling member 60 is configured to permit axial displacement (i.e., lateral movement along the longitudinal axis 25 of catheter 28) and angular deflection of the distal portion 13D in proportion to the pressure on the distal tip end 30. Measurement of the displacement and deflection gives an indication of the pressure and thus helps to ensure that the correct pressure is applied during ablation.

An electromagnetic or magnetic field is transmitted by an internal field generator MF housed in the distal portion 13D for sensing and detection by a first sensor 17 assembly housed in the proximal portion 13P. In the illustrated embodiment, the first sensor assembly 17 includes sensor coils S1, S2 and S3 located in the proximal portion 13D of the distal section 13. Each of these coils is generally parallel with the Z axis or longitudinal axis 25. The three coils are all located in a first axial section at different azimuthal angles about the longitudinal axis 25 or Z axis, where an axial plane is defined herein as a plane perpendicular to the catheter longitudinal or Z axis and an axial section is defined herein as being contained within two axial planes of the catheter. The three coils may be spaced azimuthally 120 degrees apart at the same radial distance from the axis.

Axial displacement and/or angular deflection of the distal portion 13D relative to the proximal portion 13P gives rise to a differential change in the signal outputs by the coils S1, S2 and S3, depending on the direction and magnitude of deflection, since one or two of these coils move relatively closer to the field generator MF. Compressive displacement of the distal portion 13D gives rise to an increase in the signals from each of coils S1, S2 and S3. Changes in the sensing of the magnetic field by generator MF causes the coils S1, S2 and S3 to generate electrical signals, with amplitudes that are indicative of such axial displacement and/or angular deflection. A signal processor 36 receives and processes the signals generated by the coils S1, S2 and S3, in order to derive an indication of the pressure exerted by the distal section 13 on the endocardium 70.

For the purpose of generating position data or coordinates, a driver circuit 38 in console 34 drives external magnetic field generators, for example, F1, F2 and F3, to generate magnetic fields in the vicinity of the body of patient 24 and define an external frame of reference The generators F1, F2 and F3 are comprised of coils, which are placed below the patient's torso at known positions external to the patient. These coils generate magnetic fields within the patient's body in a predefined working volume that contains heart 22.

A second sensor assembly 18 is housed in the proximal portion 13P, proximal of the first sensor assembly 17, to respond to the field generators F1, F2 and F3 and generate electrical signals. In the illustrated embodiment, the sensor assembly 18 includes at least two miniature sensor coils Sx and Sy wound on air coils. The coils have generally mutually orthogonal axes with each other and with at least one coil of the first sensor assembly 17, for example, the coil S1. Accordingly, the coil Sx is aligned with an X axis and the coil Sy is aligned with a Y axis, and both coils are orthogonal to the coil S1 aligned with the Z axis within an (X,Y,Z) coordinate system.

The two coils Sx and Sy are located in a second axial section (e.g., proximal of the first axial section of the first sensor assembly 17) at different azimuthal angles about the longitudinal axis 25 or Z axis, where an axial plane is defined herein as a plane perpendicular to the catheter longitudinal or Z axis and an axial plane is defined herein as being contained within two axial planes of the catheter. The two coils may be spaced azimuthally 120 degrees apart from each other and relative to the sensor coil S1 of the first sensor assembly 17, at the same radial distance from the axis.

Electromagnetic or magnetic fields are generated by the external field generators F1, F2, F3 and sensed by the sensor coils S1, Sx and Sy for detecting position of the catheter. The magnetic fields created by the field generators F1, F2 and F3 cause the coils S1, Sx and Sy to generate electrical signals, with amplitudes that are indicative of the position of the distal section 13 relative to the fixed frame of reference of field generators F1, F2 and F3. In one embodiment, the three field generators F1, F2 and F3 generates a magnetic field composed of three differently-oriented field components. Each of these field components is sensed by each sensor coil S1, Sx and Sy, each of which produces a signal composed of three components.

As shown in FIG. 1, the signal processor 36 of the console 34 processes these signals from the coils S1, Sx and Sy in order to determine the position coordinates of the distal section 13, typically including both location and orientation coordinates. A similar method of position sensing is implemented in the above-mentioned CARTO system and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, all of whose disclosures are incorporated herein by reference.

Signals from the sensors of the first sensor assembly 17 and the second sensor assembly 18 are transmitted to the signal processor 36 via leads. In accordance with a feature of the present invention, selected sensors from the first sensor assembly 17 and the second sensor assembly 18 are serially connected and share a common lead for transmitting their signals to the signal processor. In the illustrated embodiment of FIG. 3, leads 63, 64A and 65A extend respectively from the sensors S1, S2 and S3. The lead 63 extends from the sensor S1 to the signal processor 36. The lead 64A extends from the sensor S2 to the sensor Sx, serially connecting these sensors. The lead 65A extends from the sensor S3 to the sensor Sy, serially connecting these sensors.

As described above, each of the sensors S1, S2 and S3 generates signals representative of pressure (including axial displacement and angular deflection) of the distal section 13 obtained from sensing of the magnetic field generated by the internal field generator MF. As also described above, each of the sensors S1, Sx and Sy generates signals representative of position of the distal section obtained from sensing of each magnetic field generated by the external field generators F1, F2 and F3.

Accordingly, the lead 63 transmits to the signal processor 36 signals generated by the sensor S1 representative of pressure. The lead 64B transmits to the signal processor 36 both signals generated by the sensor S2 representative of pressure and signals generated by the sensor Sx representative of position. The lead 65B transmits to the signal processor 36 both signals generated by the sensor S3 representative of pressure and signals generated by sensor Sy representative of position. The resulting combined signals transmitted by leads 64B and by 65B create common sums which may be separated by electronic filtering where operating frequencies of position and force sensing are suitably separated in frequency space, as understood by one of ordinary skill in the art.

As such, the signal processor 36 is advantageously connected to only three leads, namely, 63, 64B and 65B for receiving signals from the five sensors for position and pressure sensing compared to the typical five or six leads of a conventional catheter with five or six position and pressure sensors. Moreover, the leads 64A and 65A serially connecting paired sensors are significantly shorter in length.

Each lead is time-consuming and expensive to manufacture and assemble in a catheter. Moreover, leads occupy space in a space-constrained catheter. Leads are also susceptible to breakage. Having a reduced number or length of leads transmitting signals to the signal processor provides a number of benefits, including reduced catheter production time, increased total catheter yield, and reduced production costs.

It is understood that different pairings of sensors for serial wiring or connection are provided by the present invention. In alternate embodiments, for example, the sensors S1 and Sx, and the sensors S2 and Sy may be serially connected, or the sensors S3 and Sx and the sensors S1 and Sy may be serially connected. For the sensors S1, S2, S3, Sx and Sy, there are six possible permutations of pairing, of which there may be one serially connected pair or two serially connected pairs in the distal section 13.

Because the coil of the generator MF in the distal portion 13D is radially symmetrical, it is well suited for on-axis alignment with the longitudinal axis 25 of the catheter. However, it is understood that the coil may also be off-axis as desired or appropriate, with the further understanding that tilting the coil off-axis will both improve certain coil(s) and degrade other coil(s) of mutually orthogonal sensors.

It is also understood that the coils of the first and second sensor assemblies 17 and 18 may be of any suitable size and shape provided they conform to packaging constraints within the distal section 13 of alignment and/or mutual orthogonality. Conventional pressure sensors tend to be cylindrical, that is, longer and narrower, because of Z axis alignment with the generator MF within the distal section, whereas conventional X and Y position sensors tend to be more elliptical so as to maintain mutual orthogonality with the Z position sensor and conformity with the packaging constraints of the distal section. In the disclosed embodiment of the present invention, the sensors S1, S2 and S3 are configured more as a conventional pressure sensor and thus are relatively longer and narrower, whereas the sensors Sx and Sy are configured more as conventional position sensors and thus are more elliptical. Position sensors and pressure sensors are described in U.S. Pat. No. 6,690,963 and U.S. Publication No. 20090138007, the entire disclosures of which are incorporated herein by reference. In the illustrated embodiment, the sensor coils S1, S2 and S3 are configured as position sensors, and the sensor coils Sx and Sy are configured as pressure sensors.

The magnetic fields generated by each field generator F1, F2, F3 and MF are distinguishable with regard to different parameters, including frequency, phase and/or time, and the signals generated by each sensor coil S1, S2, S3, Sx and Sy from measuring the magnetic field flux resulting from these distinguishable magnetic fields are similarly distinguishable. Frequency, phase and/or time multiplexing is applied as appropriate or desired. For example, the current to pressure-sensing field generator MF may be generated at a selected frequency in the range between about 16 kHz and 25 kHz, while position field generators F1, F2 and F3 are driven at different frequencies The signal processor 36 processes these signals in order to determine data, including (i) the position coordinates of the distal section 13, typically including both location and orientation coordinates, and (ii) axial displacement and angular deflection of the distal section 13. The signal processor 36 may comprise a general-purpose computer, with suitable front end and interface circuits for receiving signals from catheter 28 and controlling the other components of console 34. The processor may be programmed in software to carry out the functions that are described herein. The software may be downloaded to console 34 in electronic form, over a network, for example, or it may be provided on tangible media, such as optical, magnetic or electronic memory media. Alternatively, some or all of the functions of processor 36 may be carried out by dedicated or programmable digital hardware components. Based on the signals received from the catheter and other components of system 20, processor 36 drives a display 42 to give operator 26 visual feedback regarding the position of distal end 30 in the patient's body, as well as axial displacement and angular deflection of the distal tip of the catheter, and status information and guidance regarding the procedure that is in progress.

The processor 36 receives these signals via the leads 63, 64B and 65B extending through catheter 28, and processes the signals in order to derive the location and orientation coordinates of the distal section 13 in this fixed frame of reference, and to derive pressure information, including axial displacement and angular deflection of the distal section. The disposition of the coils S1, S2, S3, Sx and Sy and pressure exerted on the distal portion 13D of the distal section 13 can be calculated from the characteristics of the fields, such as strength and direction, as detected by the coils. Thus, the field generators F1, F2, F3 and MF and the sensing coils S1, S2, S3, Sx and Sy cooperatively define a plurality of transmitter-receiver pairs, wherein each such pair includes one field generator and a coil as elements of the pair, with each coil disposed at a different position or orientation from the other coils. By detecting the characteristics of field transmissions between the elements of the various pairs, the system de-convolves position and pressure data from the serially-connected sensors to deduce information relating to the disposition of the distal section 13 in the external frame of reference as defined by the field generators F1, F2, and F3 and information relating to pressure exerted on the distal section MF as sensed within the magnetic field generated by field generator MF. The position information can include the position of the distal section 13, the orientation of the distal section 13, or both. As understood by one of ordinary skill in the art, the calculation of position information relies upon the field generators F1, F2 and F3 being positioned in known positions and orientations relative to one another, and the calculation of pressure based on axial displacement and angular deflection relies upon the field generator MF and the sensing coils S1, S1 and S3 being in known positions and orientations relative to each other.

The field generating coils F1, F2, F3 and MF are one type of magnetic transducer that may be used in embodiments of the present invention. A "magnetic transducer," in the context of the present patent application and in the claims, means a device that generates a magnetic field in response to an applied electrical current and/or outputs an electrical signal in response to an applied magnetic field. Although the embodiments described herein use coils as magnetic transducers, other types of magnetic transducers may be used in alternative embodiments, as will be apparent to those skilled in the art.

Various other configurations of the coils in the sensing assemblies may also be used, in addition to the configuration shown and described above. For example, the positions of the field generator MF and the coils S1, S2 and S3 may be reversed, so that that field generator coil MF is in the proximal portion 13D, proximal of joint 54, and the sensor coils are in the distal portion 13D. As another alternative, coils S1, S2 and S3 may be driven as field generators (using time- and/or frequency-multiplexing to distinguish the fields), while field generator coil MF serves as the sensor. The sizes and shapes of the transmitting and sensing coils in FIG. 3 are shown only by way of example, and larger or smaller numbers of coils may similarly be used, in various different positions, so long as one of the assemblies comprises at least two coils, in different radial positions, to allow differential measurement of joint deflection.

In accordance with another feature of the present invention, while the coils Sx and Sy are orthogonal to and not aligned with the axis of the miniature field generator MF, its magnetic dipole field lines allow detection by the orthogonal coils Sx and Sy. While the coils Sx and SCy may sense a relatively weaker magnetic field by the field generator MF, compared to the coils S1, S2 and S3 because of their respective orientation relative to the field generator MF, there is sufficient sensitivity for the purpose of sensing Shaft Proximity Interference, that is, detection as to whether changes in the magnetic field of the field generator MF as sensed by the coils S1, S2 and S3 are due to physical distortion of the distal section 13 resulting from engagement with tissue or merely magnetic interference from adjacent catheters or metal or ferrous objects.

The present invention advantageously uses signals from the sensors Sx and Sy as a "back up" or "error check". During manufacturing and assembly of the catheter 28, the signals of sensors Sx and Sy generated in response to the internal field generator MF without disturbance from any adjacent catheter or metal objects are calibrated and stored in memory in the console 34. Although these signals are weaker than those generated by the sensors S1, S2 and S3 in response to the internal field generator MF, these signals by Sx and Sy carry unique signatures or characteristics. Thus, when the catheter 28 is in use with the internal field generator MF generating a magnetic field that is sensed by the sensing coils S1, S2 and S3 for determining pressure, the sensing coils Sx and Sy of the second sensor assembly 18 sensing the magnetic fields of the external field generators F1, F2 and F3 are also sensing the magnetic field by the internal field generator MF. The signal processor 36 receives signals from the sensors Sx and Sy and identifies those signals resulting from the magnetic field of the internal field generator MF (versus those resulting from the magnetic field of the external field generators F1, F2 and F3) and compares them to the calibrated signals stored in memory. If the signal processor 36 detects a discrepancy between those signals and the calibrated signals, the console 34 outputs an indication of the discrepancy to the operator and may issue a visual and/or audio alarm.

In one embodiment, a pressure calibration is performed on the distal section 13 during manufacturing and production. By identifying deformation characteristics of the resilient coupling member 60, applying known magnitudes of force on the distal portion 13D at a variety of selected angles (e.g., compressive loads, axial loads, etc.) and measuring axial displacement and angular deflection, a calibration file on the signals that may be generated by the sensors S1, S2 and S3 in response to the magnetic field generated by the internal field generator MF is compiled as a first file and stored in memory. Simultaneously, a calibration file on the signals that may be generated by the sensors Sx and Sy in response to the magnetic field generated by the internal field generator MF is compiled as a second file and stored in memory.

With the catheter in use in a patient's body, the signal processor 36 receives signals from the sensors S1, S2 and S3 in response to internal field generator MF and references those signals against the first file stored in memory to obtain axial displacement and angular deflection data for outputting catheter pressure data to the operator. Advantageously, the signal processor 36 is also receiving signals from the sensors Sx and Sy that include signals in response to the internal field generator MF and referencing those signals against the second file for detecting and identifying discrepancies.

Accordingly, the present invention includes a method of calibrating a catheter for detecting interference with magnetic field sensing caused by presence of a second catheter or other metal or ferrous object, comprising:

1) Providing a catheter with a first sensor and a second sensor with both first and second sensors adapted to respond to a magnetic field generated by a field generator.

2) Driving the field generator to enable the first and second sensors to generate calibration signals
3) Applying forces of axial displacement and angular deflection on the catheter.
4) Calibrating the calibration signals from the first sensor to create a first calibration file and calibrating the calibration signals from the second sensor to create a second calibration file, including:
   a. Applying forces of axial displacement and angular deflection to the catheter.
   b. Store in memory data representative of signals generated by the first sensor in response to forces applied to the catheter.
   c. Store in memory data representative of signals generated by the second sensor in response to forces applied to the catheter.

The present invention also includes a method of detecting interference with magnetic field sensing in a first catheter caused by presence of a second catheter or other metal or ferrous object, comprising:
1) Providing a catheter with a first sensor and a second sensor with both first and second sensors adapted to respond to a magnetic field generated by a field generator.
2) Driving the field generator to enable the first and second sensors to generate calibration signals.
3) Applying forces of axial displacement and angular deflection on the catheter.
4) Calibrating the calibration signals from the first sensor to create a first calibration file and calibrating the calibration signals from the second sensor to create a second calibration file, including:
   a. Applying forces of axial displacement and angular deflection to the catheter.
   b. Store in memory data representative of signals generated by the first sensor in response to forces applied to the catheter.
   c. Store in memory data representative of signals generated by the second sensor in response to forces applied to the catheter.
5) When the catheter is in use, driving the field generator to enable the first and second sensors to generate data signals.
6) Comparing the data signals from the second sensor to the calibration signals in the second calibration file.

The method of detecting may further include:
7) Determining whether a discrepancy exists between the data signals of the second sensor and the calibration signals in the second calibration file.
8) If a discrepancy is determined, providing an indication to user of the discrepancy.

It is understood that detection of discrepancy can be performed with or without serially connected sensors. That is, discrepancy detection uses two sets of sensors, for example, the first sensor assembly 17, namely, sensors S1, S2 and S3, and the second sensor assembly 18, namely, sensors Sx and Sy in order to have a comparative indication. Where there are serially connected sensors between the first and second sensor assemblies, the system can deconvolve the signals and data as needed.

The preceding description has been presented with reference to certain exemplary embodiments of the invention. Workers skilled in the art and technology to which this invention pertains will appreciate that alterations and changes to the described structure may be practiced without meaningfully departing from the principal, spirit and scope of this invention. It is understood that the drawings are not necessarily to scale. Accordingly, the foregoing description should not be read as pertaining only to the precise structures described and illustrated in the accompanying drawings. Rather, it should be read as consistent with and as support for the following claims which are to have their fullest and fairest scope.

What is claimed is:

1. A catheter for use with a catheterization system having a plurality of external magnetic field generators, each generating a position-data magnetic field, the catheter comprising:
    a flexible tubing; and
    a distal section configured for engagement with patient tissue, the distal section having a proximal portion and a distal portion, and comprising:
        an internal magnetic field generator positioned in one of the proximal or distal portions, the internal magnetic field generator generating a pressure-data magnetic field;
        a first plurality of pressure sensing elements and a second plurality of position sensing elements positioned in the other of the proximal and distal portions, the first plurality of pressure sensing elements configured to sense the pressure-data magnetic field and generate signals representative of data relating to pressure exerted on the distal section when engaged with tissue, the second plurality of position sensing elements configured to sense each of the position-data magnetic fields and generate signals representative of data relating to a position of the distal section;
        a first lead serially connecting at least one pair of one of the first plurality of pressure sensing elements and one of the second plurality of position sensing elements; and
        a flexible joint between the proximal portion and the distal portion, the flexible joint comprising a resilient coupling member between the internal magnetic field generator in the proximal or distal portion of the distal section and the first plurality of pressure sensing elements and the second plurality of position sensing elements in the other of the proximal or distal portion of the distal section.

2. The catheter of claim 1, wherein the resilient coupling member is configured to allow axial displacement and angular deflection between the proximal and distal portions of the distal section.

3. The catheter of claim 1, wherein the resilient coupling member comprises a coil spring.

4. The catheter of claim 1, wherein the resilient coupling member comprises a tubular piece of elastic material having a helical cut along a portion of a length of the tubular piece.

5. The catheter of claim 1, wherein the resilient coupling member comprises a polymer, a plastic or a superelastic alloy.

6. The catheter of claim 1, wherein the resilient coupling member comprises a silicone polymer or a polyurethane.

7. The catheter of claim 1, wherein the resilient coupling member comprises a superelastic alloy of nickel and titanium.

8. The catheter of claim 1, wherein the resilient coupling member is configured to permit axial displacement and angular deflection of the distal portion of the distal section in proportion to a pressure exerted on a distal tip end of the distal portion of the distal section.

9. The catheter of claim 1, wherein the first plurality of pressure sensing elements is three or less.

10. The catheter of claim 1, wherein the second plurality of position sensing elements is three or less.

11. The catheter of claim 1, wherein the first plurality of pressure sensing elements comprises a first plurality of pressure sensing coils, and the second plurality of position sensing elements comprises a second plurality of position sensing coils.

12. The catheter of claim 11, wherein the first plurality of pressure sensing coils comprises elliptical pressure sensing coils.

13. The catheter of claim 11, wherein the second plurality of position sensing coils comprises cylindrical position sensing coils.

14. The catheter of claim 1, wherein the magnetic field generator is in the distal portion of the distal section, and the plurality of first pressure sensing elements and the plurality of second position sensing elements are in the proximal portion of the distal section.

15. The catheter of claim 1, wherein the magnetic field generator is in the proximal portion of the distal section, and the plurality of first pressure sensing elements and the plurality of second position sensing elements are in the distal portion of the distal section.

16. A catheter for use with a catheterization system having a plurality of external magnetic field generators, each generating a position-data magnetic field, the catheter comprising:
  a flexible tubing; and
  a distal section configured for engagement with patient tissue, the distal section having a proximal portion and a distal portion, and comprising:
    an internal magnetic field generator positioned in one of the proximal or distal portions, the internal magnetic field generator generating a pressure-data magnetic field;
    a first plurality of pressure sensing coils and a second plurality of position sensing coils positioned in the other of the proximal and distal portions,
    the first plurality of pressure sensing coils configured to sense the pressure-data magnetic field and generate signals representative of data relating to pressure exerted on the distal section when engaged with tissue, each of the pressure sensing coils of the first plurality being generally parallel with a longitudinal axis of the catheter;
    the second plurality of position sensing coils configured to sense each of the position-data magnetic fields and generate signals representative of data relating to a position of the distal section; and
  a first lead serially connecting at least one pair of one of the first plurality of pressure sensing coils and one of the second plurality of position sensing coils.

17. The catheter of claim 16, wherein each of the position sensing coils in the second plurality are orthogonal to each other and to the pressure sensing coils in the first plurality.

18. The catheter of claim 16, wherein the internal magnetic field generator is a transmitting coil axially aligned with a longitudinal axis of the catheter, and the pressure sensing coils of the first plurality are aligned with the internal magnetic field generator.

19. The catheter of claim 16, wherein the pressure sensing coils in the first plurality are located in a first axial section at different azimuthal angles about a longitudinal axis of the catheter, the first axial section being contained within two axial planes of the catheter, the two axial planes being generally perpendicular to the longitudinal axis of the catheter.

20. The catheter of claim 19, wherein the first plurality of pressure sensing coils comprises three pressure sensing coils spaced azimuthally about 120 degrees apart at a generally same radial distance from the longitudinal axis of the catheter.

* * * * *